United States Patent [19]
Gluskin

[11] Patent Number: 5,782,750
[45] Date of Patent: Jul. 21, 1998

[54] ENDOSCOPY CONTROL END AND BIOPSY CHANNEL SHIELD

[76] Inventor: Lawrence E. Gluskin, 623 Raintree Rd., Buffalo Grove, Ill. 60089

[21] Appl. No.: 812,423

[22] Filed: Mar. 6, 1997

[51] Int. Cl.⁶ .................................................. A61B 1/04
[52] U.S. Cl. .......................................... 600/119; 128/857
[58] Field of Search ................................ 600/105, 121, 600/122, 123, 124, 125, 119, 135, 153, 154, 186, 203, 220; 128/849, 850, 851, 852, 853, 857

[56] References Cited

U.S. PATENT DOCUMENTS

| | | | |
|---|---|---|---|
| 1,459,313 | 6/1923 | Reislet et al. | 600/135 X |
| 3,144,020 | 8/1964 | Zingale | 600/119 |
| 3,674,016 | 7/1972 | Leucci | 128/4 |
| 4,022,194 | 5/1977 | Banez | 128/4 |
| 4,834,068 | 5/1989 | Gottesman | 128/4 |
| 4,848,322 | 7/1989 | Dash et al. | 128/4 |
| 4,958,623 | 9/1990 | Rocco | 128/7 |
| 5,024,212 | 6/1991 | Bonnet et al. | 128/4 |
| 5,123,402 | 6/1992 | Vandenbossche et al. | 128/7 |
| 5,498,244 | 3/1996 | Eck | 604/198 |
| 5,527,280 | 6/1996 | Goelz | 604/96 |
| 5,542,435 | 8/1996 | Kelly et al. | 128/846 |
| 5,554,098 | 9/1996 | Yabe et al. | 600/121 |
| 5,569,159 | 10/1996 | Anderson et al. | 600/114 |

*Primary Examiner*—Beverly M. Flanagan
*Attorney, Agent, or Firm*—Leydig, Voit & Mayer, Ltd.

[57] ABSTRACT

An endoscope shield provides a barrier between a biopsy port and an endoscopist. The shield has a shield portion and attachment portion. The shield portion is flat and angled away from and toward the control end of the endoscope. The shield portion is located so that it separates a biopsy channel port from a barrel located on the endoscope. The shield is angled so that it overlies the barrel of the endoscope and therefore the hand of an endoscopist when placed on the barrel. A component of the shield portion extends normal to the axis of the barrel to adequately provide a barrier between the biopsy channel port and the endoscopist's head during examination procedures. An adjustable clamp releasably attaches the shield to the endoscope.

15 Claims, 3 Drawing Sheets

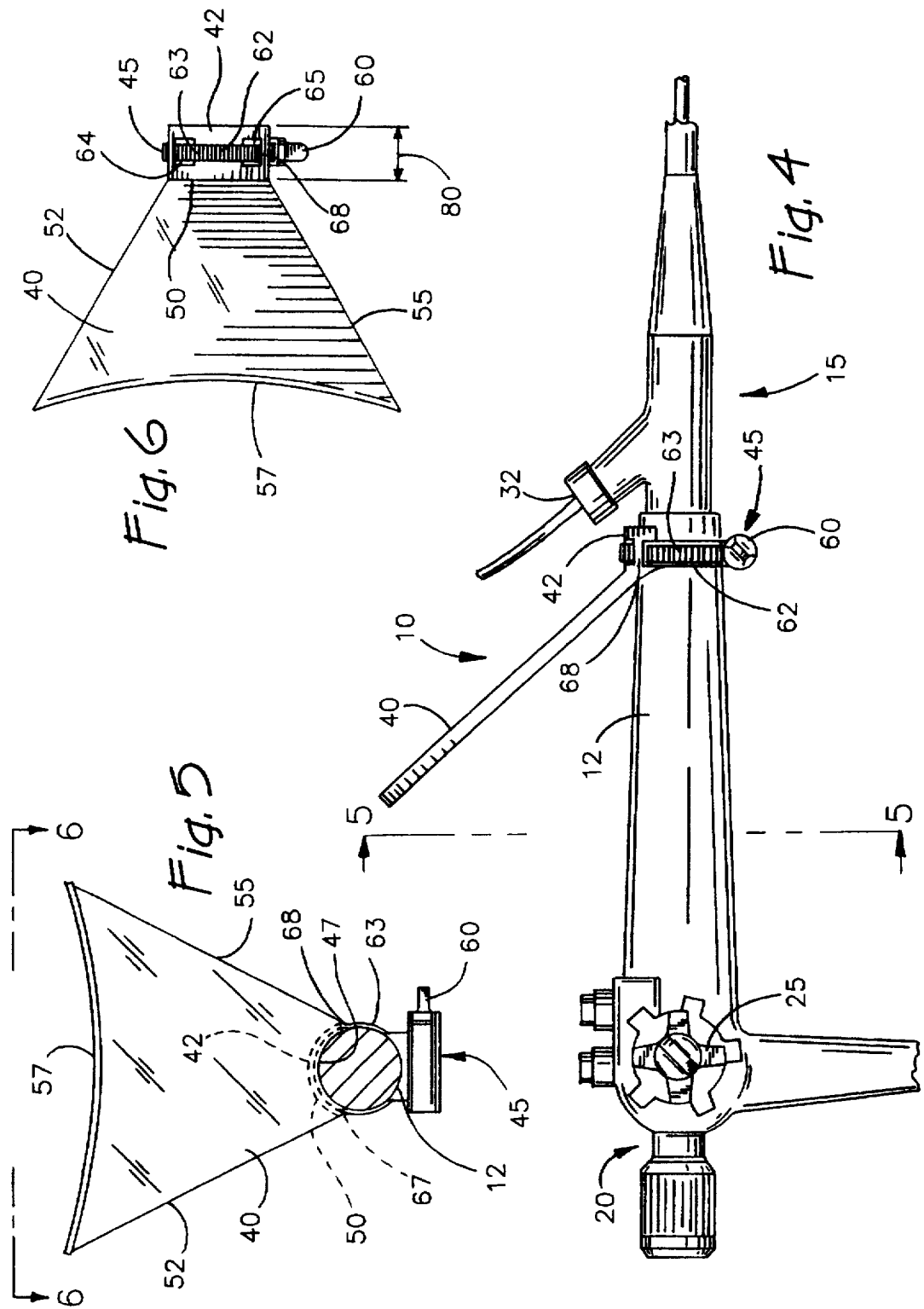

ENDOSCOPY CONTROL END AND BIOPSY CHANNEL SHIELD

FIELD OF THE INVENTION

This invention relates to endoscopy and, more specifically, to apparatus used to protect against the transmission of fluids between patient and physician during endoscopic procedures.

BACKGROUND OF THE INVENTION

Physicians use endoscopes in lieu of surgery to internally examine patients and to take biopsy samples. Accordingly, a proximal end of an endoscope has a hollow, flexible shaft which is inserted into a patient through a bodily opening. A distal or control end remains outside the patient and carries the controls for manipulating the proximal end. A cylindrical barrel is provided near the control end for gripping the endoscope. In video endoscopes, video components extend through the shaft and communicate with a monitor screen. Non-video endoscopes typically use fiber optic components to communicate with an eyepiece located at the control end.

The shaft of an endoscope also houses a biopsy channel through which biopsy tools may be passed. A biopsy port is typically located between the proximal and distal ends of the endoscope which allows biopsy tools to be inserted into and removed from the biopsy channel. The biopsy port is sealed with a rubber cap. A small opening in the cap allows the biopsy tool to pass through and enter the biopsy channel.

During the examination and biopsy procedures noted above, the physician must work in close proximity to the endoscope biopsy port. In examination procedures using both video and non-video endoscopes, the physician holds the barrel of the endoscope in one hand raised roughly chest high. In this position, the biopsy port of the endoscope is in close proximity to the physician's hand, face and body. Non-video endoscopes further require the physician to bring the distal or control end of the endoscope near the physician's head for viewing through the eyepiece. The physician's face is therefore brought even closer to the biopsy port when using a non-video endoscope. During biopsy procedures using both video and non-video endoscopes, the physician must grip the barrel of the endoscope with one hand while a biopsy tool is inserted or withdrawn. Thus the physician must place his or her hand near the biopsy port during biopsy procedures.

Procedures involving a conventional video and nonvideo endoscopes having biopsy channels subject the endoscopist to increased risk of transmission of disease from the patient. Frequently, patient secretions, such as blood, feces, and sputum, are splashed from the biopsy tool during examination and biopsy procedures. These fluids may, therefore, come in contact with the physicians face and hands.

The procedure to carry out biopsy operations presents an additional risk of transmitting germs and disease. Biopsy tools may slip during insertion or removal into the biopsy port and strike the endoscopist's hand, with the risk of puncturing the skin, even when gloves are worn. As a result, the endoscopist is subject to possible contamination and risk of serious disease. In addition, the biopsy tool may become contaminated if it contacts the physician's hand or gloves. The patient is, therefore, at risk if the contaminated tool is subsequently inserted into the patient. As a result, both the patient and physician are at risk during biopsy procedures.

Accordingly, a device is desired which reduces the risk of infection while performing endoscopic procedures. Proposals have been made to install shields on endoscopes usually near the control of the endoscope. The proposals involve shields which appear to be bulky or difficult to attach to the endoscope, or are capable of attachment in only one position on the endoscope. The present inventor is aware of no successful application of such shields on commercially available endoscopes.

SUMMARY OF THE INVENTION

Accordingly, it is an object of the present invention to provide practical apparatus to more effectively reduce the transmission of disease during endoscopic procedures.

More particularly stated, it is an object of the present invention to provide apparatus which is shaped and can be located such that it separates the biopsy port of an endoscope from the head and hands of an endoscopist during endoscopic procedures.

In that regard, it is an object of the present invention to provide a shield for an endoscope which has a component projecting along a first axis which protects the eyes and head of an endoscopist and a component along a second axis which protects the hand of an endoscopist.

It is yet another object of the present invention to provide an endoscope shield that is adjustable for attachment to a variety of endoscopes and in a number of locations on an endoscope.

Yet another object of the present invention is to provide a shield which requires little axial space for attaching the shield to an endoscope having a cylindrical barrel.

To achieve these and other objectives, a shield is provided for separating a biopsy port from the operating (i.e. control) end of an endoscope. The shield comprises a base, shield portion, and attachment means. The base closely conforms to a barrel of the endoscope and occupies minimal axial space on the barrel. The shield portion is flat and extends at an angle away from the endoscope and toward the control end. The angle of the shield portion allows it to overlie the barrel of the endoscope. In addition, the angled shield portion projects sufficiently away from the endoscope so that it protects the endoscopist's head. Attachment means are provided for adjustably and releasably attaching the shield to the endoscope.

Another embodiment of the present invention comprises an endoscope with integrally formed shield. Instead of having means for releasably attaching the shield, the shield portion is permanently attached to and provided with the endoscope. The shield portion used in this embodiment may be identical to that described in the preferred embodiment.

These and other objects and advantages of the invention will become more apparent from the following detailed description when taken in conjunction with the accompanying drawings.

BRIEF DESCRIPTION OF THE DRAWINGS

FIG. 4 is a side elevation of the shield attached to an endoscope.

FIG. 5 is a top view of the shield attached to an endoscope taken along reference line 4—4 of FIG. 3.

FIG. 6 is a top view of the shield taken along reference line 5—5 of FIG. 4.

Figure 1:
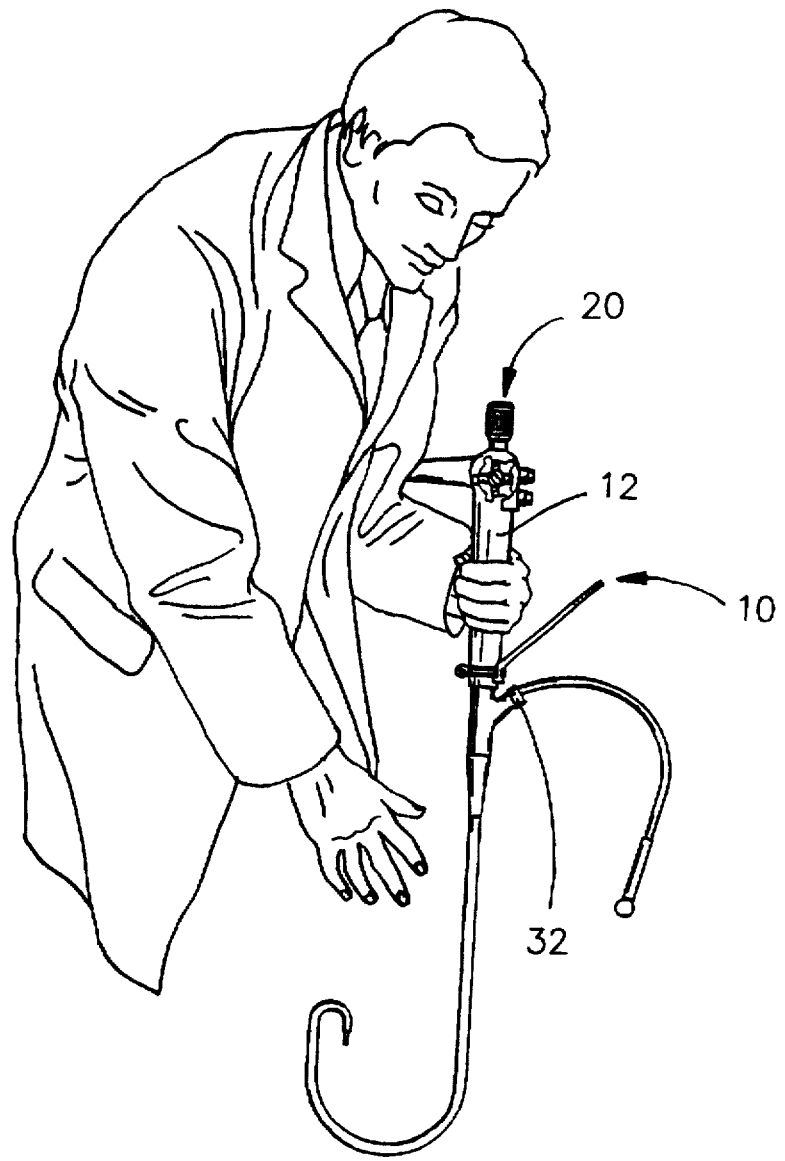
FIG. 1 shows the position of an endoscope during an examination procedure and the location of the shield in accordance with the present invention.

While the invention is susceptible of various modifications and alternative constructions, certain illustrated embodiments thereof have been shown in the drawings and will be described below in detail. It should be understood, however, that there is no intention to limit the invention to the specific forms disclosed, but on the contrary, the intention is to cover all modifications, alternative constructions and equivalents falling within the spirit and scope of the invention as defined by the appended claims.

DETAILED DESCRIPTION OF THE PREFERRED EMBODIMENT

Figure 2:
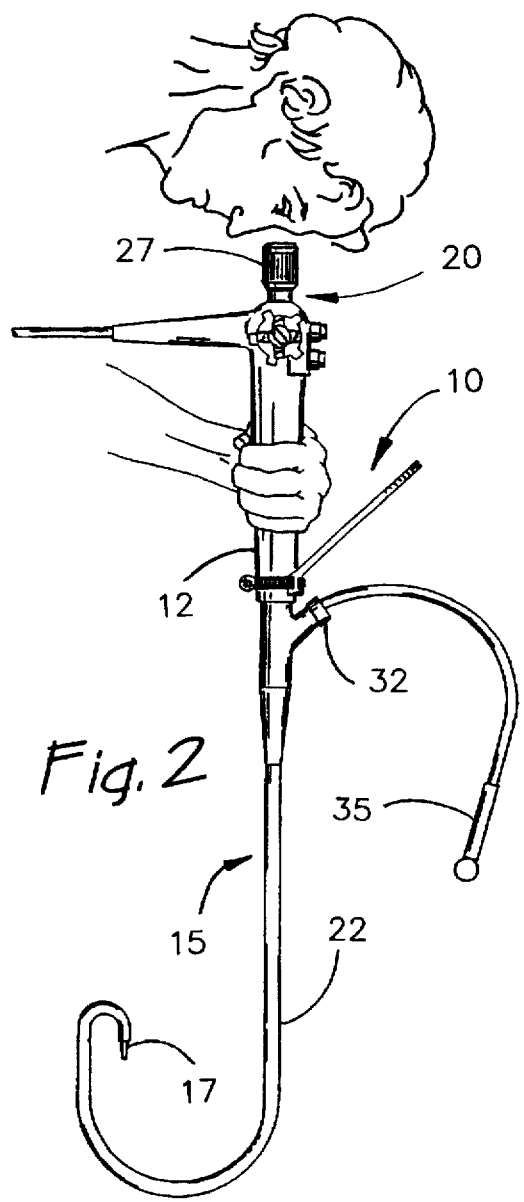
FIG. 2 shows a close-up of the position of a non-video endoscope during an examination procedure and the location of the shield in accordance with the present invention.
Figure 7:
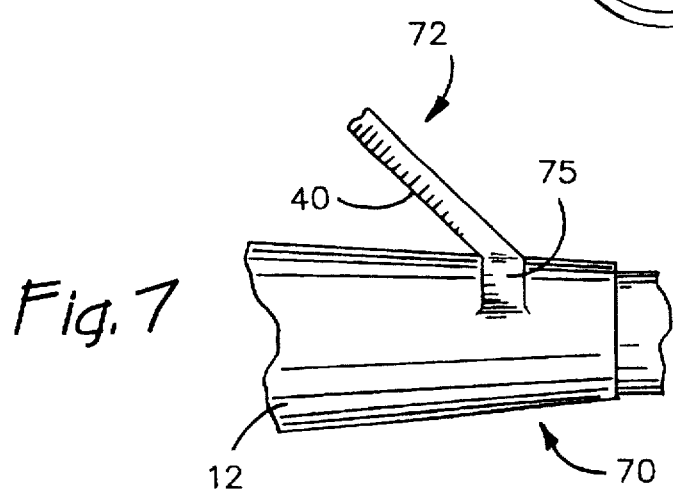
FIG. 7 is a cutaway side elevation of an endoscope with integrally provided shield according to one embodiment of the present invention.

For purposes of illustration, the invention has been shown in FIGS. 1, 2, and 7 as incorporated in a shield 10 attached to the barrel 12 of an endoscope 15. While the endoscope 15 does not itself constitute part of the present invention, further description is provided to better understand the present invention. As shown in FIG. 1, the endoscope 15 comprises proximal and distal ends 17, 20. The proximal end 17 has a flexible, hollow shaft 22 which may be inserted into a bodily opening of a patient. The distal or control end 20 has controls 25 for manipulating the shaft 22. The control end of the non-video endoscope further has an eyepiece 27 (FIGS. 1 and 2). A biopsy port 32 is located between the proximal and distal ends 17, 20 of the endoscope 15. The biopsy port 32 allows biopsy tools 35 to be inserted through and withdrawn from a biopsy channel in the shaft 22. A barrel 12 is located between the biopsy port 32 and the control end 20. The barrel 12 extends along an axis and provides an area for gripping the endoscope 15.

Figure 3:
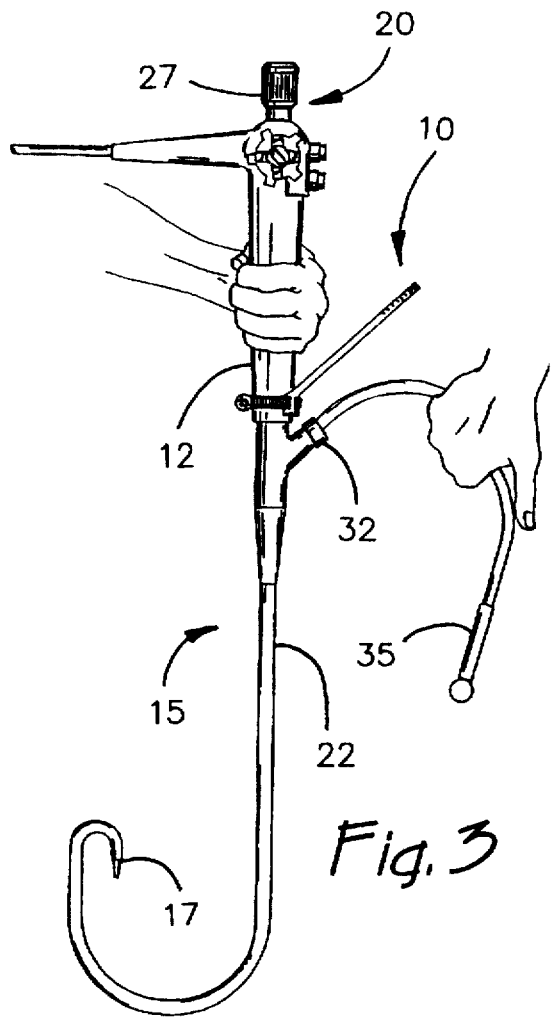
FIG. 3 shows the position of an endoscope during a biopsy procedure and the location of the shield in accordance with the present invention.

In accordance with one objective of the present invention, a shield 10 is attached to the endoscope in such a position and orientation as to provide substantial protection to the head and hand of an endoscopist. As best illustrated in FIGS. 1 and 2, the shield 10 is shown protecting the face and hand of an endoscopist during an examination procedure. The shield 10 also protects the physician's hand during biopsy procedures (FIG. 3). During examination procedures using a non-video endoscope, as best shown in FIG. 2, the eyepiece 27 of the endoscope 15 is brought to the physician's eye. The shield 10 attached to the endoscope 15 has a component normal to the axis of the barrel sufficient to provide a barrier between the biopsy port 32 and the endoscopist, thereby preventing fluids expelled from the patient from directly reaching the endoscopist's eyes and face. During a biopsy procedure, the physician holds the endoscope by gripping the barrel 12 while inserting or withdrawing a biopsy tool 35 from the biopsy port 32 (FIG. 3). The shield 10 has a component projecting parallel to the axis of the barrel 12 which partially overlies the barrel 12 and protects the hand of the endoscopist during a biopsy procedure. As illustrated in FIG. 3, the shield 10 separates the biopsy port 32 from the physician's hand, thereby reducing the risk of contact between the biopsy tool 35 and the physician's hand. The risk of inadvertent puncture of the physician's hand during insertion and withdrawal of the biopsy tool is thus substantially avoided.

In the video endoscope shown in FIG. 1, the endoscope is held with the axis of the barrel 12 disposed substantially vertical during examination and biopsy procedures. The shield 10 has a component projecting along the axis of the barrel 12 toward the control end 20 of the endoscope which protects the endoscopist's hand. The shield also has a component projecting normal to the axis of the barrel 12 sufficient to provide a barrier for protecting the physician's head from the biopsy port 32.

As illustrated in FIGS. 1-3, the shield 10 is preferably located on an end of the barrel 12, near the biopsy port 32. In this position, the effective area of the shield 10 will be maximized while providing adequate grip space on the barrel 12.

FIGS. 4-6 more particularly show a shield 10 in accordance with the present invention. The illustrated shield 10 comprises a shield portion 40, a base 42, and attachment means 45.

The base 42 is provided for seating the shield 10 on the barrel 12 of the endoscope 15. According to the preferred embodiment, the base 42 has an arcuately shaped seating face 47 conforming to the outside radius of the cylindrical barrel 12. The base 42 encompasses only a portion of the barrel 12 to allow easy engagement and release of the shield 10. The base 42 has a relatively small width 80 to minimize the axial extent along the barrel 12 needed to seat the shield 10. It will be appreciated that the base size allows the shield 10 to be attached at a number of locations on the endoscope 15 as is convenient to a particular application.

The shield portion 40 is attached to the base 42 and provides means for separating the biopsy port 32 from the control end 20 of the endoscope 15. According to the embodiment illustrated in FIGS. 4-6, the shield portion 40 is flat and angled away from and toward the control end 20 of the endoscope 15. When the shield 10 is attached to the endoscope 15, the barrel 12 and the shield portion 40 define an angle such that the shield portion 40 overlies part of the barrel 12 (FIGS. 3 and 4). The angle is preferably 45 to 50 degrees.

It will be appreciated that the angled configuration of the shield portion 40 performs at least two functions. First, the component of the shield portion 40 projecting normal to the axis of the barrel 12 protects the eyes and forehead of the endoscopist (FIGS. 1 and 2). Second, the component of the shield portion 40 parallel to the axis of the barrel 12 overlies the barrel 12 of the endoscope 15, thereby protecting the hand of the endoscopist.

In the preferred embodiment, the shield portion 40 has a truncated triangular shape defined by four sides. As shown in FIG. 5, the first side 50 is arcuately shaped and joins the shield portion 40 to the base 42. Second and third sides 52, 55 start at opposing ends of and extend outwardly from the first side 50, thereby diverging from the base 42. A fourth side 57 connects the divergent ends of the second and third sides 52, 55. The shield is made of a thermoplastic material. In the preferred embodiment, the thermoplastic material is relatively rigid and capable of being molded. The shield will thus be made in a single piece. The barrel preferably has a degree of flexibility so that tightening of the band clamp, at a portion where the radius of the barrel and the radius of the endoscope are somewhat different, will tend to conform the base to the shape of the barrel. A preferred material is polystyrene.

Attachment means 45 are provided for selectively and releasably securing the shield 10 to the endoscope 15. In the preferred embodiment, the attachment means 45 comprises an adjustable clamp 62 adaptable to a range of barrel diameters. In addition, the adjustable clamp allows the shield 10 to be attached at various positions along the endoscope 15, including the preferred position. The clamp 62 preferably has thumbscrew means 60 for adjusting the diameter of the clamp 62.

The clamp 62 comprises an elongate arcuate band 63 which engages the base 42 of the shield. Preferably, as shown in the drawings, the band projects through a pair of apparatus 64 and 65 such that the lower portion of the band 63 grips the barrel of the endoscope, while the upper portion of the band grips the base 42. The apparatus 64 and 65 provide a pair of retaining arms 67 and 68 which hold the clamp in its appropriate position on the shield, even when the shield is removed from the endoscope.

To install the shield on the endoscope, the thumb screw 60 can be rotated so that the end of the band 63 is free of the clamp 62, whereupon the barrel of the endoscope can be inserted into the clamp and the clamp reconnected and tightened with the shield in the appropriate location. Alternatively, if the band 63 is of sufficient diameter open, it can be inserted over the control end in at least some types of endoscopes, slid into position, then tightened. However, the ability of the clamp to remain in place on the endoscope yet open so as to allow the endoscope barrel to be inserted, then simply reconnected and tightened, is believed to be a significant advantage for ease of installation and removal. This is particularly important in situations where the unit is to be disassembled before a sterilization or autoclaving.

In another embodiment of the present invention, an endoscope 70 is provided with an integral shield 72. In this embodiment shown in FIG. 6, the shield 72 is formed directly on the barrel 12. The shield 72 is permanently attached to the endoscope 70 and, therefore, no clamping means are required. A base 75 and shield portion 40 are provided similar to the above embodiment, thereby achieving the benefits noted above.

From the foregoing, it will be apparent that the present invention describes a new and improved shield for an endoscope. The shield has a base which conforms to the barrel of an endoscope and occupies little axial space on the barrel. The size of the base allows the shield to be attached to numerous positions on an endoscope. The clamp is configured to allow for ease of installation, removal and adjustment. The shield portion, when placed in the preferred position, provides multiple protections. The shield provides a barrier between the biopsy port and the head of the endoscopist when placed near the control end. This beneficially protects the endoscope user from fluids which may be sprayed or splashed from the body during a procedure. In addition, the shield protects the hand of an endoscopist when it is placed on the barrel of the endoscope. Such protection is useful when, for example, the endoscopist is inserting or manipulating a biopsy tool. If the biopsy tool were to slip during insertion into or removal from the biopsy channel, it would strike the shield rather than the hand of the endoscope user. Accordingly, both the endoscopist and the patient are protected from inadvertent transmission of germs and disease during biopsy procedures. The shield may be provided with attachment means for releasably attaching the shield to a range of barrel diameters and endoscope locations, or may be integrally provided with an endoscope and therefore permanently affixed.

What is claimed is:

1. A shield adapted to be releasably attached to an endoscope barrel, the barrel extending along an axis and located on the endoscope between a control end and a biopsy port, the shield comprising a base, a shield portion, and attaching means, the base comprising an arcuate flange conforming to the outer surface of the barrel and having a relatively small width extending along the barrel axis to allow attachment to the barrel at a point between the biopsy port and the control end of the endoscope, the shield portion joined to and extending from the base, the shield portion having a first component projecting normal to the axis of the barrel to protect the face of an endoscope user during examination procedures, the shield portion having a second component projecting parallel to the axis of the barrel overlying part of the barrel and protecting the hand of the endoscope user during examination and biopsy procedures, and the shield portion being made of semi-rigid thermoplastic material.

2. The shield of claim 1 wherein the second component of the shield portion is flat and, when attached to the endoscope, defines an angle between the shield portion and the barrel, the angle directed away from the barrel and toward the control end of the endoscope.

3. The shield of claim 2 wherein the angle between the second component of the shield portion and the barrel is 45 to 50 degrees.

4. The shield of claim 2 wherein the second component of the shield portion is substantially triangular in shape.

5. The shield of claim 4 wherein the shape of the second component of the shield portion is defined by four sides, a first, radially curved side adapted to conform to the base, a second side extending from one end of the base and diverging away from the endoscope, a third side extending from an opposing end of the base and diverging away from the endoscope, and a fourth side connecting free ends of the second and third sides.

6. The shield of claim 1 wherein the means for releasably attaching the shield portion to the shaft of the endoscope comprises an adjustable clamp.

7. The shield of claim 6 wherein the adjustable clamp has thumbscrew means for adjusting the clamp.

8. The shield of claim 6 in which the adjustable clamp has band and a locking means, the band encircling the barrel and being provided with means for adjusting the circumference of the clamp to engage and thereupon grip the barrel.

9. The shield of claim 8 in which the arcuate flange of the base includes a pair of slots through which the band of the clamp is passed to attach the clamp to shield.

10. The shield of claim 9 wherein the adjustment means allows the band to be removed therefrom so that the shield may be positioned over the barrel before the clamp is engaged and adjusted to thereby secure the shield in position.

11. An endoscope with integrated shield, the endoscope having a barrel extending along an axis and located on the endoscope between a biopsy port and a control end, the shield comprising a base and a shield portion, the base forming part of the barrel and comprising an arcuate flange conforming to the outer surface of the barrel and having a relatively small width extending along the barrel axis to allow positioning of the base on the barrel at a point between the biopsy port and the control head, the shield portion joining and extending from the base, the shield portion having a first component projecting normal to the axis of the barrel to protect the face of an endoscope user during examination procedures, the shield portion having a second component projecting parallel to the axis of the barrel overlying part of the barrel and protecting the hand of the endoscope user during examination and biopsy procedures, and the shield portion being made of rigid and transparent material.

12. The shield of claim 11 wherein the second component of the shield portion is flat and extends from the shaft at an angle away from and toward the control end of the endoscope.

13. The shield of claim 12 wherein the angle between the second component of the shield portion and the barrel is 45 to 50 degrees.

14. The shield of claim 13 wherein the second component of the shield portion is substantially triangular in shape.

15. The shield of claim 14 wherein the shape of the second component of the shield portion is defined by four sides, a first, radially curved side adapted to conform to the base, a second side extending from one end of the base and diverging away from the endoscope, a third side extending from an opposing end of the base and diverging away from the endoscope, and a fourth side connecting free ends of the second and third sides.

* * * * *

UNITED STATES PATENT AND TRADEMARK OFFICE
CERTIFICATE OF CORRECTION

PATENT NO.    : 5,782,750
DATED         : July 21, 1998
INVENTOR(S)   : Lawrence E. Gluskin It is certified that error appears in the above-identified patent and that said Letters Patent is hereby corrected as shown below:

In column 6, claim 2, line 1, delete "the second component of".

In column 6, claim 3, line 2, delete "second component of the".

In column 6, claim 4, line 1, delete "the second component of".

In column 6, claim 5, lines 1-2, delete "the second component of".

In column 6, claim 12, lines 1-2, delete "the second component of".

In column 7, claim 13, lines 1-2, delete "the second component of".

In column 7, claim 14, lines 1-2, delete "the second component of".

In column 7, claim 15, lines 1-2, delete "the second component of".

Signed and Sealed this

Twentieth Day of October, 1998

Attest:

BRUCE LEHMAN

*Attesting Officer*    *Commissioner of Patents and Trademarks*